US009435822B2

(12) United States Patent
Snyman

(10) Patent No.: US 9,435,822 B2
(45) Date of Patent: Sep. 6, 2016

(54) CMOS MOEMS SENSOR DEVICE

(75) Inventor: Lukas Willem Snyman, Faerie Glen (ZA)

(73) Assignee: Tshwane University of Technology, Pretoria (ZA)

( * ) Notice: Subject to any disclaimer, the term of this patent is extended or adjusted under 35 U.S.C. 154(b) by 909 days.

(21) Appl. No.: 13/378,234

(22) PCT Filed: Jun. 15, 2010

(86) PCT No.: PCT/ZA2010/000033
§ 371 (c)(1),
(2), (4) Date: Mar. 9, 2012

(87) PCT Pub. No.: WO2011/038423
PCT Pub. Date: Mar. 31, 2011

(65) Prior Publication Data
US 2012/0154812 A1    Jun. 21, 2012

(30) Foreign Application Priority Data

| Jun. 15, 2009 | (ZA) | 2009/04162 |
| Jun. 15, 2009 | (ZA) | 2009/04163 |
| Jun. 26, 2009 | (ZA) | 2009/04509 |
| Jul. 3, 2009 | (ZA) | 2009/04665 |
| Jul. 3, 2009 | (ZA) | 2009/04666 |
| Jul. 28, 2009 | (ZA) | 2009/05249 |
| Dec. 11, 2009 | (ZA) | 2009/08834 |
| May 21, 2010 | (ZA) | 2010/03603 |
| May 21, 2010 | (ZA) | 2010/03605 |

(51) Int. Cl.
*H01L 27/15* (2006.01)
*G01P 15/093* (2006.01)
*G01D 5/26* (2006.01)
*G01F 1/28* (2006.01)
(Continued)

(52) U.S. Cl.
CPC ............ *G01P 15/093* (2013.01); *G01D 5/266* (2013.01); *G01F 1/28* (2013.01); *G01N 21/7703* (2013.01);
(Continued)

(58) Field of Classification Search
CPC ...... H01L 25/167; H01L 27/00; H01L 27/15
USPC .................................................. 257/79, 83, 84
See application file for complete search history.

(56) References Cited

U.S. PATENT DOCUMENTS

| 2009/0121236 A1* | 5/2009 | Worley | 257/84 |
| 2010/0285523 A1* | 11/2010 | Pinsky et al. | 435/39 |
| 2012/0224167 A1* | 9/2012 | Sanders et al. | 356/73.1 |

FOREIGN PATENT DOCUMENTS

| WO | WO 2007/122556 A2 | 11/2007 |
| WO | WO 2010/086798 A1 | 8/2010 |

OTHER PUBLICATIONS

Snyman, L. et al. "A Dependency of Quantum Efficiency of Silicon CMOS $n^+pp^+$LEDs on Current Density", IEEE Photonics Technology Letters, vol. 17, No. 10, Oct. 2005, pp. 2041-2043.

*Primary Examiner* — Mark Tornow
(74) *Attorney, Agent, or Firm* — Merchant & Gould P.C.

(57) ABSTRACT

The present invention relates to a sensor device. More particularly, the invention relates to a CMOS-based micro-optical-electromechanical-sensor (MOEMS) device with silicon light emitting devices, silicon waveguides and silicon detectors being fabricated using current Complementary Metal Oxide Semiconductor (CMOS) technology or Silicon on Insulator (SOI) technology. According to the invention there is provided a sensor comprising: a Silicon-based light emitting structure; an integrated electro-optical mechanical interface structure that is capable to sense mechanical deflections; an integrated electronic driving and processing circuitry so as to detect physical parameters such as vibration, motion, rotation, acceleration.

9 Claims, 14 Drawing Sheets

(51) Int. Cl.
*G01N 21/77* (2006.01)
*G02B 6/12* (2006.01)
*G02B 6/42* (2006.01)

(52) U.S. Cl.
CPC ....... *G02B 6/12004* (2013.01); *G01N 21/7746* (2013.01); *G02B 6/4246* (2013.01); *H01L 27/15* (2013.01)

CMOS MOEMS SENSOR DEVICE

This application is a National Stage Application of PCT/ZA2010/000033, filed 15 Jun. 2010, which claims benefit of Serial No. 2009/04162, filed 15 Jun. 2009 in South Africa, Serial No. 2009/04163, filed 15 Jun. 2009 in South Africa, Serial No. 2009/04509, filed 26 Jun. 2009 in South Africa, Serial No. 2009/04665, filed 3 Jul. 2009 in South Africa, Serial No. 2009/04666, filed 3 Jul. 2009 in South Africa, Serial No. 2009/05249, filed 28 Jul. 2009 in South Africa, Serial No. 2009/08834, filed 11 Dec. 2009 in South Africa, Serial No. 2010/03603, filed 21 May 2010 in South Africa and Serial No. 2010/03605, filed 21 May 2010 in South Africa and which applications are incorporated herein by reference. To the extent appropriate, a claim of priority is made to each of the above disclosed applications.

INTRODUCTION

The present invention relates to a sensor device. More particularly, the invention relates to a CMOS-based micro-optical-electromechanical-sensor (MOEMS) device with silicon light emitting devices, silicon waveguides and silicon detectors being fabricated using current Complementary Metal Oxide Semiconductor (CMOS) technology or Silicon on Insulator (SOI) technology.

BACKGROUND TO THE INVENTION

The vast majority of micro-electronic devices are formed in silicon and, over the last several decades, a substantial effort has been directed to refining the reliability and manufacturability of these devices. As a result, silicon-based microelectronic devices have become dependable and inexpensive commodity items. Particularly, Complementary Metal Oxide Semiconductor (CMOS) technology has become a multi-billion industry providing the basis manufacturing technology for nearly 80° AD of all electronic commodities to society. Furthermore Silicon-on-Insulator (SOI) technology is regarded as a future basis technology for combining optoelectronics technology with mainstream electronics manufacturing technology.

To take advantage of the existing silicon-based knowledge and infrastructure, there is a great interest in integrating active optical components into CMOS and SOI silicon technologies.

Silicon, however, is an indirect band gap semiconductor material which, unlike a direct band gap semiconductor material, has low photon emission efficiency. As a result, silicon is considered a poor source of electroluminescent radiation.

Although the photon-generation mechanism is not well understood, one source of visible light from silicon is a reverse biased p-n junction under avalanche breakdown conditions.

Avalanche breakdown occurs when the p-n junction is reverse biased and the electric field across the junction accelerates electrons into having ionizing collisions with the lattice. The ionizing collisions generate additional electrons which, along with the original electrons, are accelerated into having additional ionizing collisions. As this process continues, the number of electrons increases dramatically, producing a current multiplication effect. Building on this principle, Snyman et al. in "A Dependency of Quantum Efficiency of Silicon CMOS n pp LEDs on Current Density, IEEE Photonics Technology Letters, Vol. 17, No. 10, October 2005, pp 2041-2043", have reported that the efficiency of light emission from silicon in a Silicon Light Emitting Device (Si LED) can be substantially increased by utilizing a reverse biased p-n junction with a wedge-shaped tip that confines the vertical and lateral electric field.

Sensor devices have been fabricated in discrete packages in order to measure physical parameters such as temperature, mechanical shock, motion, acceleration, rotation, light levels, fluid flow rate, counting of particles in a flow system, fluorescence and absorption of such particles. However these devices often require complex and sophisticated technology.

Although the sensor device can be formed on a hybrid module, further improvements of the sensor devices especially to integration and compactness are generally desirable in order to explore new applications of these devices.

What is therefore required is a sensor device which not only offers an easier integration into an existing commercially available manufacturing technology of CMOS, but also one which provides improved performance characteristics.

OBJECTS OF THE INVENTION

It is an object of the present invention to provide a sensor device, preferably a light emitting structure fabricated from commercially available manufacturing technology, which overcomes, at least partly, the disadvantages associated with existing sensor structures.

It is also an object of the present invention to provide a sensor device which is both novel and involves an inventive step.

SUMMARY OF THE INVENTION

According to a first aspect of the invention there is provided a sensor comprising: a Silicon-based light emitting structure; an integrated electro-optical mechanical interface structure that is capable to sense mechanical deflections; an integrated electronic driving and processing circuitry so as to detect physical parameters such as vibration, motion, rotation, acceleration.

The sensor may be is either Complementary Metal Oxide Semiconductor (CMOS) technology based or Silicon-on-insulator (SOI) based and integrated on a single chip.

The sensor may further comprise additional optical filters and a reference optical path section so as to increase the sensitivity of the device for measurements.

The sensor may further comprise a monolithically integrated wave-guiding system integrated with the silicon light emitting structure on the same chip.

The wave-guiding system may further comprise Silicon nitride, or silicon-oxinitride or an optically transparent polymer.

The sensor may further comprise a fluidic interfacing module replacing the electro-mechanical module so as to detect optical absorption, additional wavelength added or omitted elements in gaseous or fluidic samples.

According to a second aspect of the invention, there is provided a method of creating a silicon LED based sensor, wherein: enhanced light emission is created through enhanced secondary excitation processes in the silicon itself; or enhanced light emission is created through enhanced secondary excitation processes in secondary bodies having a high photonic yield and by placing the second body within reach of the secondary body; and utilizing this light emission to sense physical or fluidic change parameters as detected by creating a secondary optical path arrangement which interfaces closely with the environment and creates enhanced detection of the physical changes through either intensity modulation or phase contrast techniques.

The device utilizes low cost visible light emitters that can be integrated into the system at the chip level at micro-dimensions and that, together with fibre or glass technology and mechanical modules, can provide the measurement of the necessary physical parameter. The key cost competitive advantage in terms of manufacturing costs is achieved with the simplicity of design, simplicity in assembling and in the utilization of low cost integrated circuit integrated LEDs.

In summary, the CMOS based sensor device according to the invention comprises a body containing, a CMOS silicon-based light emitting device, one or two optical paths, an electro-mechanical or fluidic environmental interface module, a silicon detector and electronic processing circuitry electronic driving and modulation circuitry. The electro-optical module introduces a disturbance or phase shift in a optical path B, which interacts with the reference optical path A and introduces either intensity or phase shift changes at the detector. Correspondingly, physical changes such as vibration, motion, rotation, acceleration as caused by a mechanical vibrating arm, or intensity changes as caused by fluidic gases or liquids can be detected. The device can be highly integrated in a small volume of integrated circuit space utilizing standard Complementary Metal-Oxide Semiconductor (CMOS) integrated or Silicon-on-Insulator (SOI) technology

BRIEF DESCRIPTION OF THE DRAWINGS

The invention will now be described in greater detail by way of example with reference to the following drawings in which.

DETAILED DESCRIPTION OF THE INVENTION

Making now reference to the drawings, embodiments of the present invention are outlined in more detail.

Figure 1:
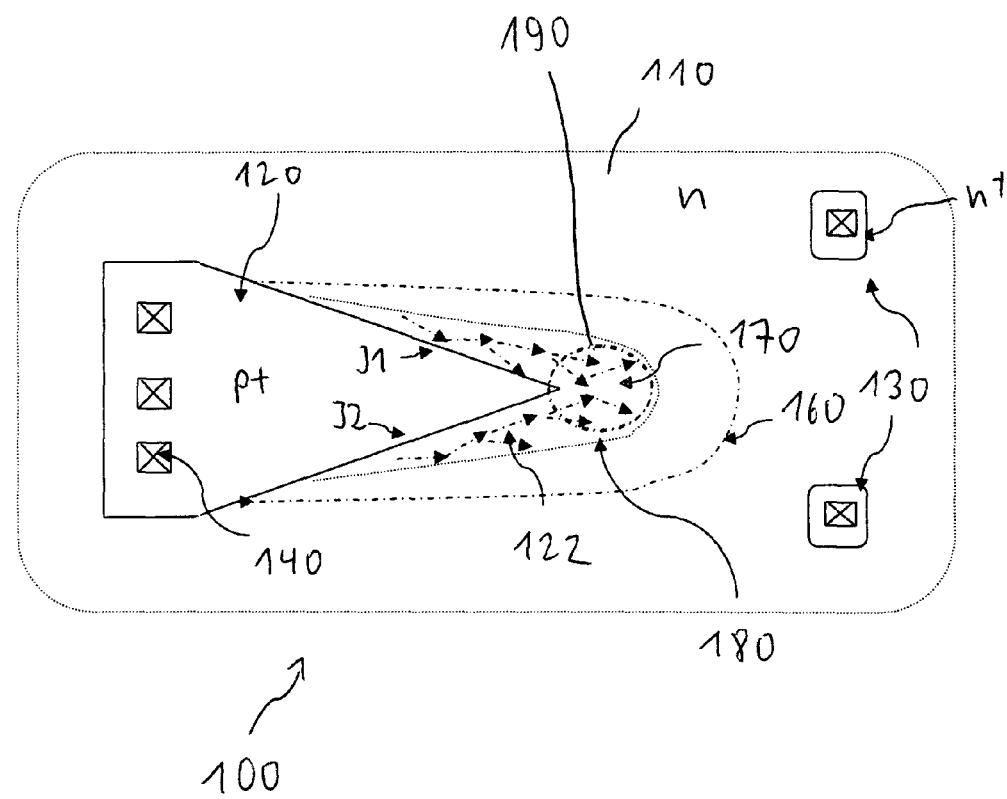
FIG. 1 is a plan view illustrating a p+nn+ version of an Enhanced Lateral Secondary Excitation Si LED in accordance with the present invention.

Enhanced versions of SiLEDs have recently been developed. FIG. 1 describes this type of device. The device 100 is constructed comprising a highly doped semiconductor region 120, with an elongated triangle and sharp point protrusion 122. This structure is placed in a semiconductor region 110 of lower doping which is sufficiently large to accommodate the maximum extended depletion region extending from the region 120 upon reverse bias along the junction periphery (junction 1 and 2 interfaces), adjacent to the elongated triangle body side. Third low resistance electrical/ohmic contact regions 130 are placed in the first, opposite and directly parallel to the maximum protrusion body length. The device is appropriately voltage biased such as to create an elongated depletion region along the periphery 140 of the second body junction towards the electrical contact body regions. Charge carriers as excited in the maximum electric field region near to the junction (p+n junction in FIG. 1) interface, now will accelerate and transverse not perpendicular to the junction interface, but will rather laterally traverse laterally along the junction 1 and 2 interfaces as indicated by the arrows in FIG. 11. Since the depletion region (up to the edge 160) is much more extended as compared to a normally oriented depletion region, the accelerated carriers will now traverse a much longer path before exiting the junction at the end of the depletion region. During their traverse path, they will undergo multiple mean free acceleration paths, each ending in a collision and ionization process of host lattice crystal atoms, defects, impurities, and or other carriers. During these interaction processes light photons are emitted, leading to a particular increase in the total light emission level from the device. It follows that the longer lateral trajectory paths, results in enhanced scattering and multiple mean free paths. This leads to an enhanced avalanche in multiplication of secondary carriers; an exponential increase in further accelerated carriers and an exponential increase in total light emission from the junction. The multiplication region is indicated by reference numeral 180, leading to a dominant light emission region 170. The excited carriers create secondary carriers that again cause new excitations and new light emission processes within the silicon itself.

By choosing the primary semiconductor body material and conductivity types of the respective bodies, and using the fact that at the multiplication and avalanching of electrons are roughly twice for that of holes in silicon, the concentration and the type of energetic carriers can be engineered. p+ n n+ type arrangement are therefore particularly suitable for yielding high intensity CMOS based LEDs.

Consequently, appropriate secondary bodies can also be placed within reach of the excited carriers so as to create light emission from either the primary or secondary excited carriers. These Si LEDs were appropriately designated as "secondary excitation Si LEDs". The structure of the device is relatively simple and can be fabricated with ease utilizing CMOS technology. A preferred positioning of such secondary bodies is shown as 190 in FIG. 1.

Figure 2:
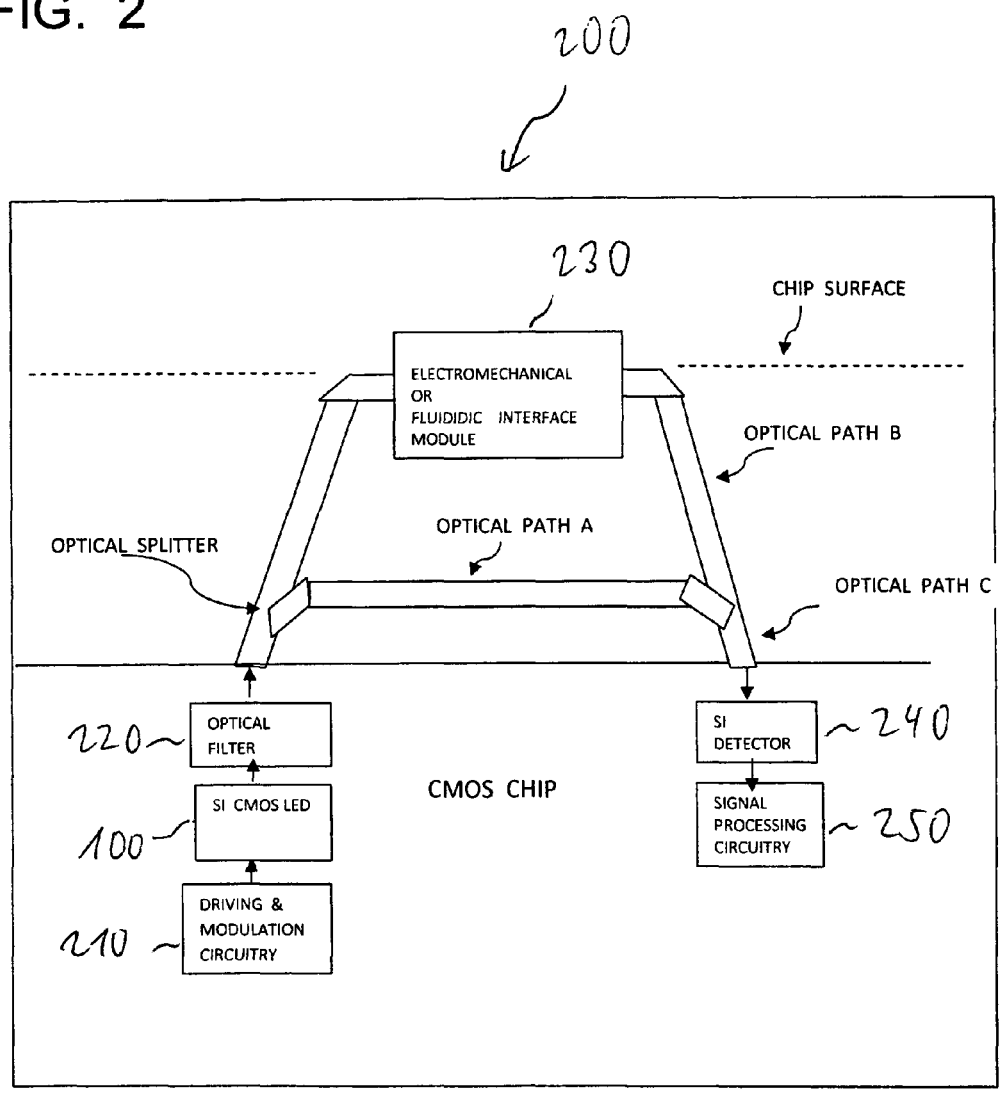
FIG. 2 is a cross-sectional view illustrating an example of a generic Si LED and CMOS technology based Micro-Optical-Mechanical-Sensor in accordance with the present invention.

FIG. 2 shows an example overview and cross-sectional view of a Si LED based CMOS MOEMS device 200 showing various sub-components in accordance with the current invention, and utilizing the SiLEDs. Using conventional CMOS fabrication technology, a Silicon Light Emitting Device (Si LED) 100 is fabricated. Appropriate driving and modulation circuitry 210 controls the optical output of the device in terms of intensity and pulse width of the LED The optical emission is (optionally) filtered using optical filter 220 in order to ensure a narrow bandwidth. The optical emission is guided along suitable optical paths A and B by means of directional emission or wave-guiding technology, using optical intensity splitting and wave-guiding techniques. Path A is used as a reference path with respect to phase and intensity, while path B is transmitted through an electro-mechanical interface or fluidic interface module 230, which introduces an intensity and/or phase change to the optical beam. This module is located either subsurface of the CMOS over-layers or it interfaces with the CMOS chip surface. The two beams is combined in beam section C, where it is fed to a silicon optical detector 240. The signal output from the detector is processed by means of appropriate signal processing circuitry 250, and then delivered in analogue or digital format to the rest of the CMOS circuitry which can successfully interpret the signal and information in terms of a physical parameter as measured.

The electro-mechanical sensor interface section is designed such that it detects mechanical vibration, motion, rotation, acceleration and introduces an intensity or phase change to optical path B. Similarly, if a fluidic interface module is used to interface either with a gas or liquid fluid, and accordingly introduces an intensity change, a phase change or a wavelength change to the optical beam in path B. The system can accordingly be utilized to sense mechanical parameters such as vibration, motion, rotation, acceleration, gas flow, gas composition or liquid flow or liquid composition. The whole arrangement is fabricated as a highly integrated module in a small section of CMOS chip. Since the system uses optical means of detection and processing, it has all the advantages as associated with optical signal processing techniques, such as highly miniaturized system, highly integrated manufacturing, low cost of manufacturing, noise immunity, and high reliability.

The electro-mechanical interface module may utilize state of the art cantilever, micro-beam deflection or disc rotation techniques. The fluidic interface module may utilize state of the art gas or fluid absorption monitoring or wave-length spectrum detection techniques utilizing optical sources and optical sensors.

The novel component of the device/arrangement is the Si LED that can be integrated into the silicon subsurface (or the chip over-layers) and that provides sufficient optical power such that the detectors can detect the optical changes as introduced by the mechanical or fluidic interface module with a sufficient signal to noise ratio, such that information can be processed and outputted to adjacent circuitry.

Figure 3:
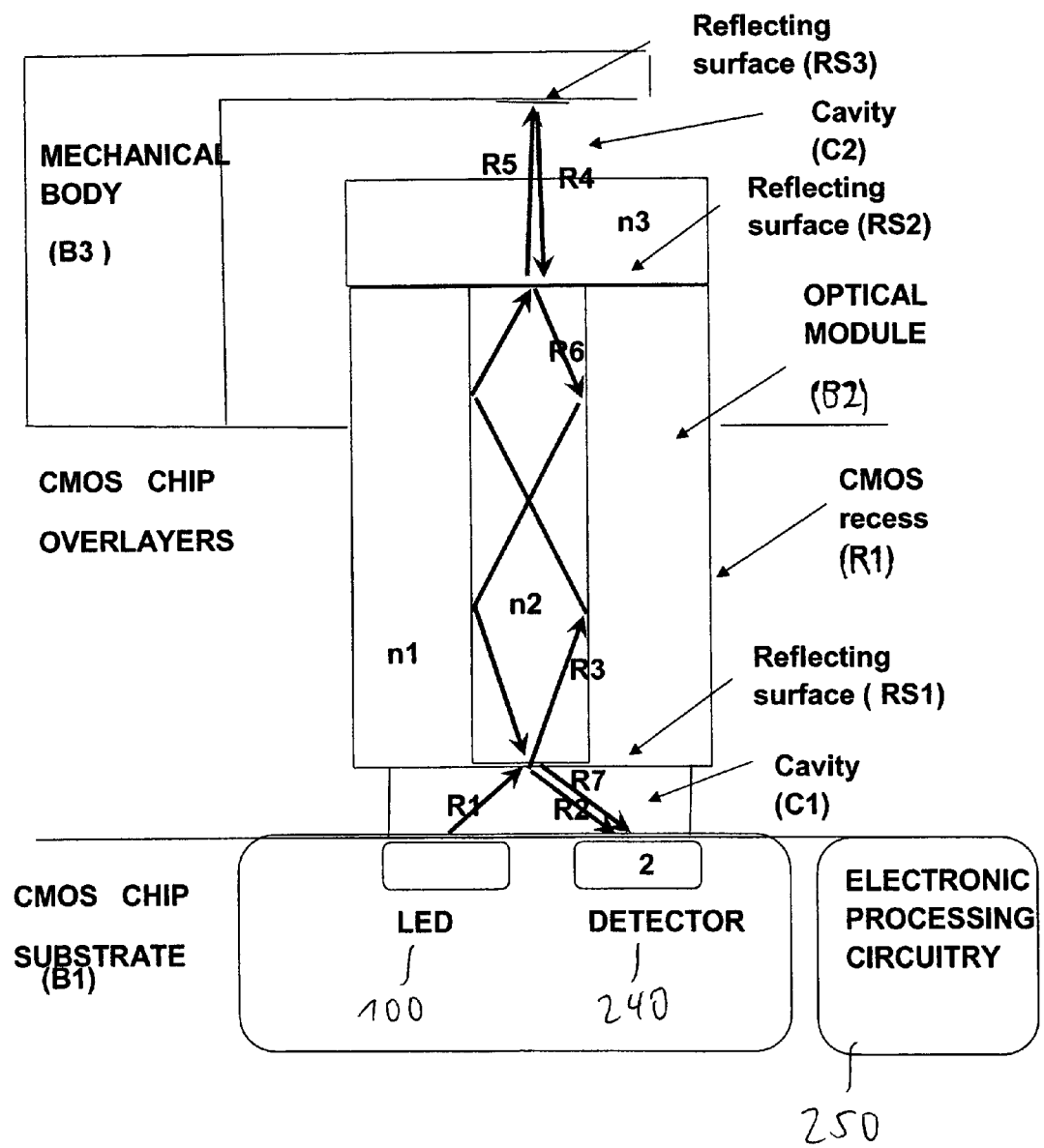
FIG. 3 is a schematic diagram showing a hybrid realization the MOEMS device as a preferred first embodiment of the invention.
Figure 4:
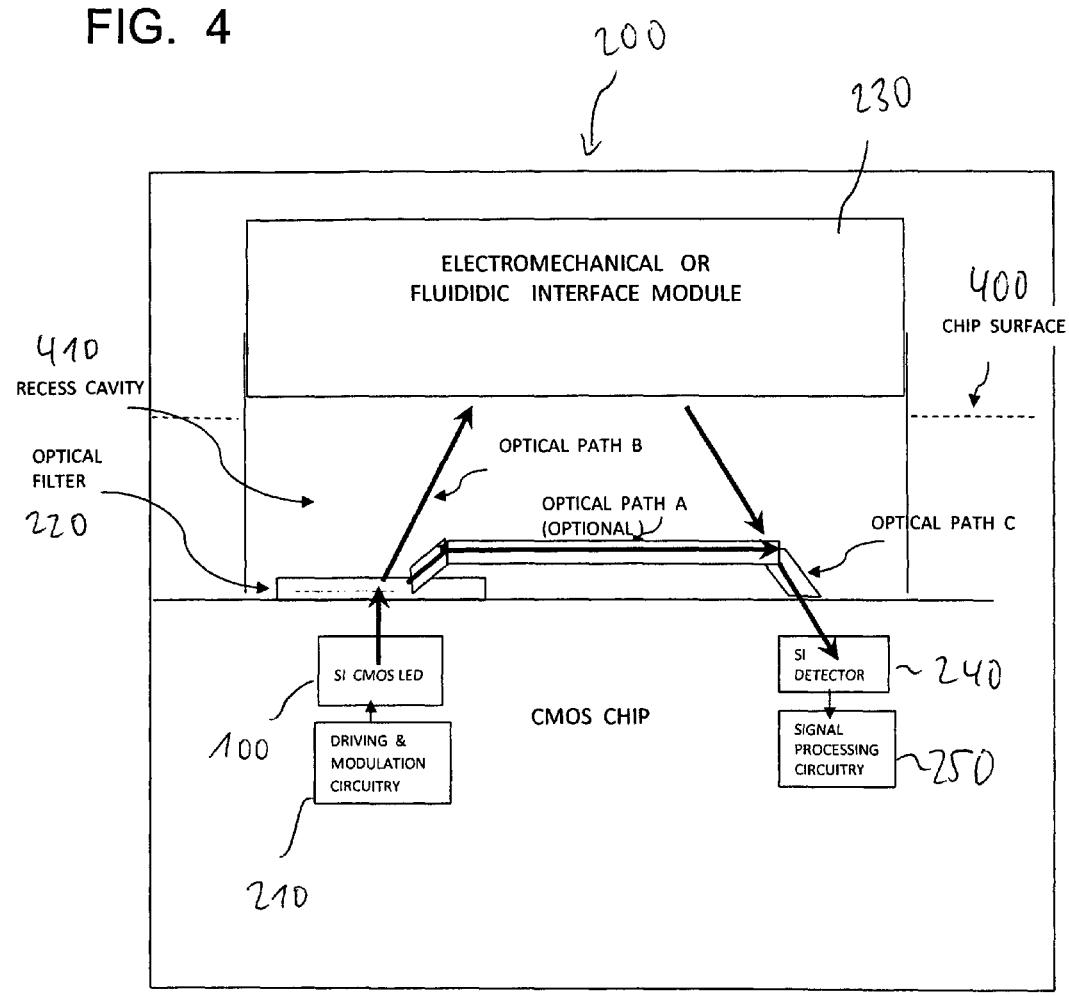
FIG. 4 is a schematic diagram showing a mixed hybrid-monolithic realization the MOEMS device as a preferred second embodiment of the invention.
Figure 5:
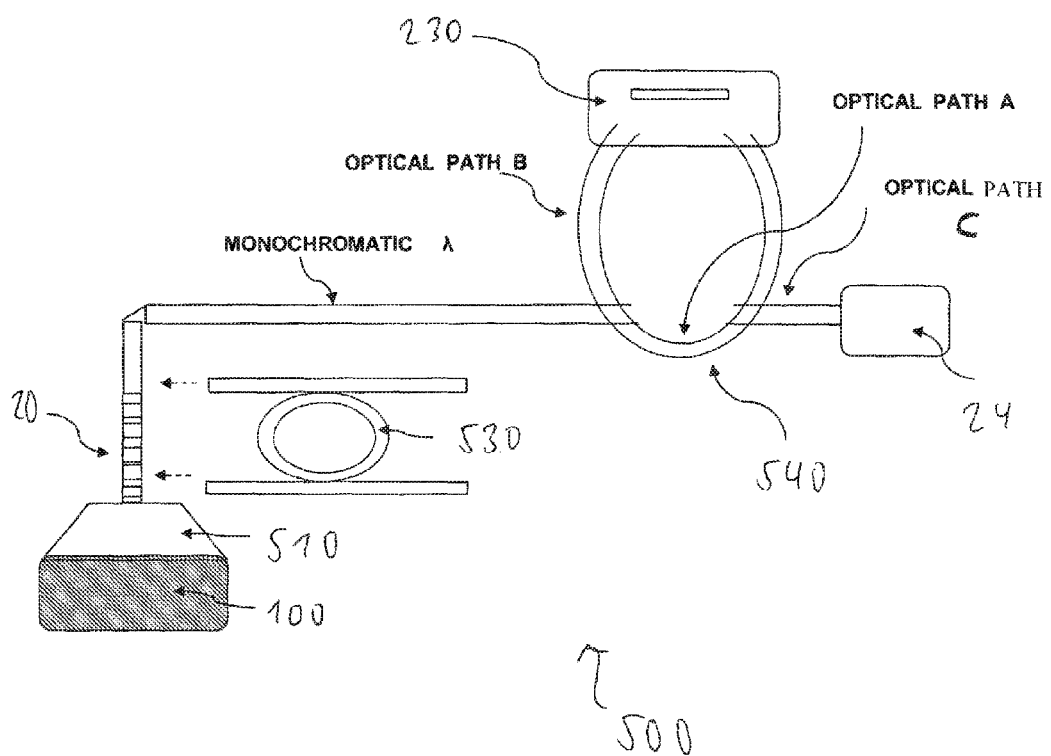
FIG. 5 is a schematic diagram showing a full monolithic realization the MOEMS device as a preferred third embodiment of the invention.

FIGS. 3 to 5 describe various preferred embodiments of the invention.

FIG. 3 is a schematic diagram showing a hybrid realization the MOEMS device as a preferred first embodiment of the invention, utilizing a mechanical module, an optical module as fabricated in a recess cavity on a CMOS chip hosting the Si LED, optical detection circuitry and appropriate driving and signal processing circuitry. FIG. 3 describes a first hybrid embodiment of the invention fabricating a recess in the CMOS over-layers, and adding various optical and mechanical modules such that a total system is realized using hybrid component and hybrid component assembling means, involving Pick and Placing of components into the recess cavity in a CMOS chip.

FIG. 3 describes the embodiment of the invention using hybrid approach of the invention. The device consist of three separate modules or bodies viz a semiconductor chip module B1, an optical module or body B2 and a mechanical module or body B3, relative to each other as shown in FIG. 4. An integrated (or embedded) light emitting diode, LED, emits light of a narrow bandwidth into the recess cavity, C1, facilitated previously in the CMOS over layers. Rays impact on a partially reflecting surface RS1. A certain percentage intensity of these rays are reflected to the integrated (or embedded) detector, DET. Another percentage of the light is refracted into optical body B2 body and follows internal reflection paths R3 as indicated in FIG. 3. At the partially reflecting surface RS2, a percentage of the light is reflected back to the chip interface according to light rays path R6. Emitting from the optical body after further refraction as, the externally reflected light interferes with the initially reflected light R2 and cause intensity change in the light reaching the detector DET. Another percentage of light at partially refracted at RS2 enters the n3 refraction index region of the optical body B2, and emits normally to this body, then travels through a second cavity C2, is reflected back at reflecting surface RS3. A percentage of this reflected light returns back into the optical body B2 and contribute to phase contrast and intensity change at the detector DET.

If the mechanical arm position changes status, the path length imposed by rays R4 and R5 will cause an intensity change in the detector. Shock, motion, acceleration or rotation of the device will all impose position changes of reflecting surface RS3 and results in intensity changes detected at the detector DET. By extending the air gap path into the secondary cavity environment, intensity changes can be detected at the detector due to various status changes in this cavity e.g. if fluid flows introduced through the cavity C2. The arm can be appropriately modified to detect fluid flow rate. If particles of high optical absorption flow through cavity C2, this will impose sharp changes in the intensity transmitted through C2 which will enable particle counts by the processing circuitry. Similarly, other properties such as absorption and fluorescence as caused by the particles can accordingly impose changes on the intensity as detected by the detector. The signals at the detector is appropriately electronically analyzed and processed for suitable interpretation by micro-processor circuitry.

FIG. 4 is a schematic diagram showing a mixed hybrid-monolithic realization the MOEMS device as a preferred second embodiment of the invention, utilizing a mechanical module, as fabricated in a recess cavity on a CMOS chip hosting the Si LED, optical detection circuitry and appropriate driving and signal processing circuitry. The optical filter and reference optical path can either be hybridly added to surface of the CMOS chip or it can be monolithically fabricated as an integral part of the CMOS chip. FIG. 4 describes a second embodiment of invention using hybridly added mechanical or fluidic interface unit into a recess cavity into a CMOS chip; and either using a hybridly added optical filter and second optical paths.

FIG. 4 gives a second embodiment of the invention using a mixed-hybrid monolithic approach. A recess is manufactured such that the chip surface 400 is sufficiently exposed so as the emit light vertically out of the chip at either a vertical or slanted direction. An appropriate optical filter 220 is fabricated at the chip-recess interface such that only a narrow bandwidth in wavelength of the optical emission of SiLED 100 is transmitted into the recess cavity 410. The electro-mechanical or fluidic interface module 230 is located inside the recess cavity, or partially inside the recess cavity 410 or totally outside the recess cavity. The optical filter 220 may be fabricated using monolithic layer fabrication technology, or it may be pick-and-placed positioned separately into the cavity.

The optical radiation following path A towards and back from the electromechanical or fluidic interface module 230 is of narrow bandwidth or monochromatic nature which will enhance phase contrast and eventually contribute towards enhanced intensity changes as detected by the detector. An optional optical path A may be fabricated utilizing monolithic, waveguide based or other hybrid techniques. This addition may enhance the phase contract and intensity changes at the detector 240 as a result of changes introduced by the electro-mechanical or fluidic interface module.

FIG. 5 describes a third completely monolithic embodiment of the invention utilizing all CMOS fabrication technology. FIG. 5 is a schematic diagram showing a full monolithic realization the MOEMS device 500 as a preferred third embodiment of the invention, utilizing a mechanical module, as fabricated in a recess cavity on a CMOS chip. The Si LED 100, the wave-guiding circuitry, filtering components and phase contrast enhancement components are all fabricated monolithically as an integral part of the CMOS chip.

A large area silicon light emitting device supplies sufficient optical power to a monolithically integrated wave guiding system on the chip or section thereof. The optical power is transferred to the waveguides through an appropriate optical coupler 510. The coupled optical radiation in the fibre is then filtered by either a Bragg grating filter 520 or (optional) ring resonator filter 530 (or any other state of the art wave-guiding filtering means) such that a very narrow band radiation (as close to mono-chromatic as possible) is obtained. The optical radiation is then split into two waveguide paths, path A and path B, as in an un-balanced Mach Zender phase detector 540. In the optical path B, the optical radiation is exposed to the electro-mechanical or fluidic interface module 230, which introduces a phase change according to the selected physical detection parameter. This phase change causes a resulting intensity change in the final optical path C before it is fed into the optical detector 240.

Figure 6:
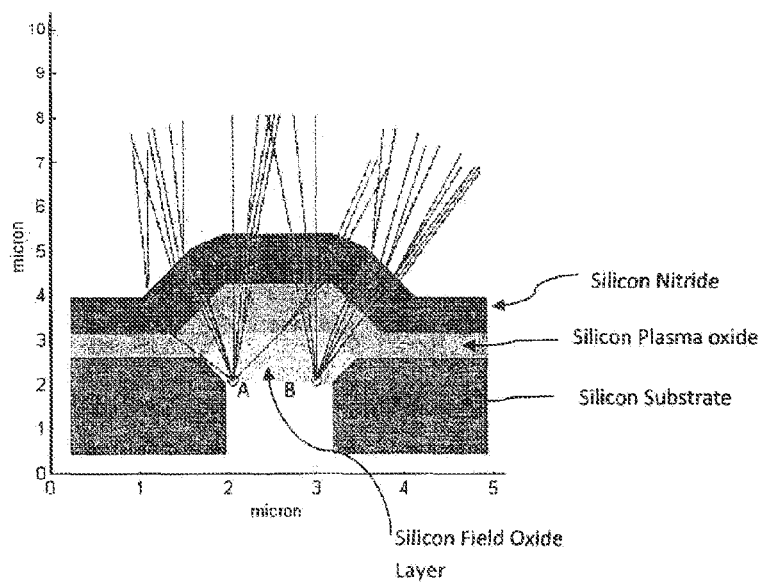
FIG. 6 shows a schematic diagram showing the typical layers used in CMOS integrated circuit technology.
Figure 7:
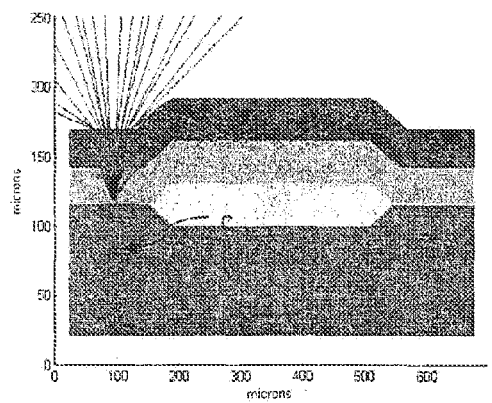
FIG. 7 shows a schematic diagram showing an optical splitting structure by positioning the optical source and utilising CMOS integrated circuit technology.
Figure 8:
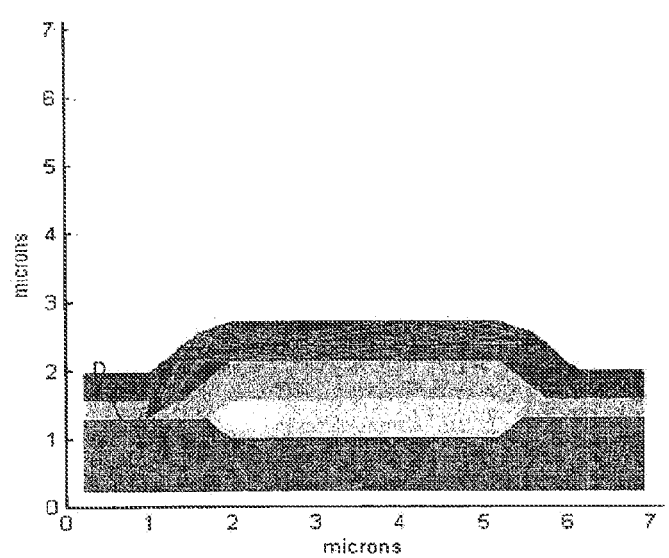
FIG. 8 shows a schematic diagram showing achievement of complete wave-guiding in an optical splitting structure by positioning the optical source and utilising CMOS integrated circuit technology.

FIGS. 6 to 8 describe various beam directing, optical spitting and wave-guiding techniques that can be used in the optical paths A, B and C.

FIG. 6 shows a schematic diagram showing the typical layers used in CMOS integrated circuit technology viz (1) the optically transparent $SiO_2$ field oxide layer, (2) the inter-metallic plasma deposited oxide layers; and (3) the silicon nitride ($Si_3N_4$) passivation layer. Two optional optical emission points, A and B, are shown in the CMOS chip and the focusing and directional emission properties of the structure are illustrated.

FIG. 6 shows the schematic diagram showing the typical layers as used in CMOS integrated circuit technology for optical application purposes. The optically transparent layers are SiO2 field oxide layer, silicon nitride (Si3N4) passivation layer and inter-metallic plasma deposited oxide layers which are all deposited as over-layers on the silicon substrate. In this case a small section of field oxide is fabricated using above 0.35 micron CMOS technology, so as to create a curvature in the overlying plasma oxide and silicon nitride layers. The lateral length of the structure was reduced and the position of the optical source was placed at an optimized point at the silicon substrate-field oxide interface in the centre of the structure. The optical launch angles for the rays were chosen in the range, 30°-150°. The design can be implemented to include a circular nature of the centre field oxide region. When the source is placed at position A, a clear focusing of almost all rays emitting vertically from the structure is observed. The focusing and beam directional changes are caused by the change in refractive indexes of the various layers viz 1.4 for silicon oxide, 1.55 for silicon plasma oxide and 2.4 for silicon nitride.

When the source is placed at position B, a clear directional emission of the radiation towards a slanted 45 degree angle is observed, also with some focusing or converging of optical rays present.

FIG. 7 shows a schematic diagram showing an optical splitting structure by positioning the optical source at position, C, in CMOS integrated circuit technology. The layer definitions are the same as in FIG. 6. FIG. 7 demonstrates a structure that can be used to create optical splitting of the optically radiated power in more or less equal percentages in two different paths. In this case a 0.3 micron field oxide layer and 1 micron silicon passivation and plasma deposited layers were assumed as commonly encountered in 0.35 micron CMOS technology. One portion of the radiation emitted out of the structure into air, and the other radiation was emitted laterally into the silicon nitride layer.

FIG. 8 shows a schematic diagram showing achievement of complete wave-guiding in an optical splitting structure by positioning the optical source at position, D, in CMOS integrated circuit technology. The layer definitions are the same as in FIG. 6. FIG. 8 demonstrates optimized lateral wave-guiding longitudinally along the silicon nitride layer for a very high proportion of the totally emitted Si LED radiation. The plasma oxide layer thickness has been reduced locally and the optical emission point in the generated structure is positioned near the "bird beak" point in the silicon oxide layer. The initial rays launch angles ranging from 34°-76° couple effectively into the silicon nitride layer. Due to the lower refractive indexes of both the plasma and field oxide below the layer and the refractive index of air above the layer, the radiation is effectively guided along the silicon nitride layer.

A very important aspect related to the invention is that silicon nitride and silicon oxi-nitride is essentially transparent for radiation for radiation higher than 600 nm. This is substantially lower than the absorption edge of silicon which lies at approximately 850-950 nm which imply that the radiation can still be effectively detected using standard CMOS detector technology. Silicon nitride therefore offers itself as a most suitable candidate for generating electro-optic and waveguide structures in CMOS integrated circuitry. If longer wavelength Si LEDs are used as optical sources, it implies that an "all-silicon" wave-guiding and MOEMS systems can be very effectively realized in CMOS technology.

Figure 9:
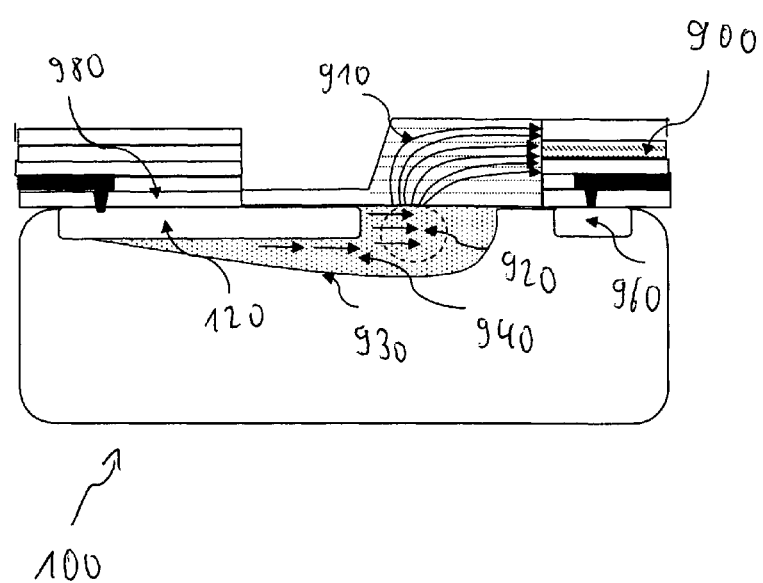
FIG. 9 shows a schematic diagram showing achievement of effective optical coupling of optical radiation from a Lateral Multiplication and Secondary Excitation Si LED into silicon nitride or other wave-guide layers as situated in the CMOS chip over-layers, by utilizing graded index optically transparent layers immediately above the Si LED emission point.
Figure 10:
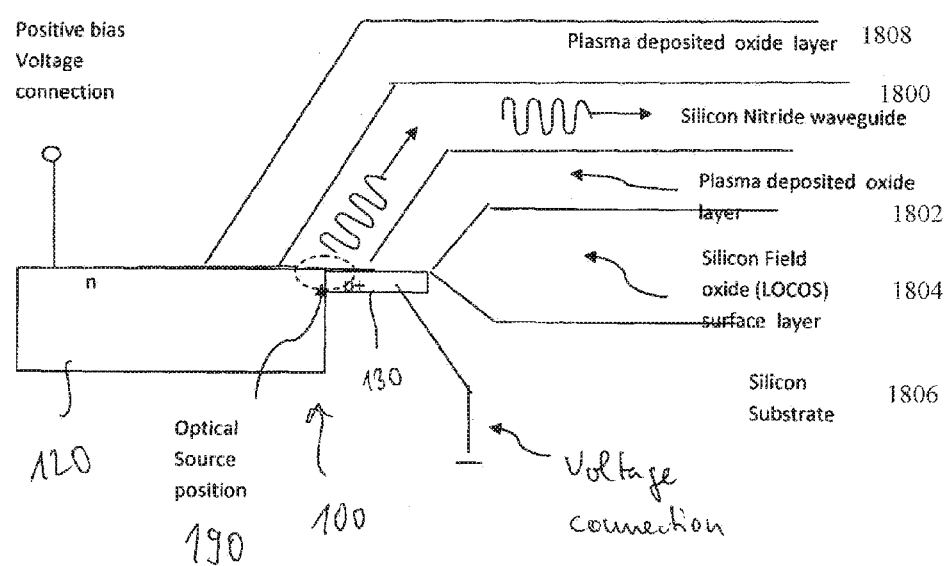
FIG. 10 to FIG. 12 shows some further preferred embodiments using above 0.35 micron CMOS technology.

FIGS. 9 and 10 describe details of optical coupling technology from the Si LED to the optical paths A, B and C.

FIG. 9 shows a schematic diagram showing achievement of effective optical coupling of optical radiation from a Lateral Multiplication and Secondary Excitation Si LED into silicon nitride or other wave-guide layers as situated in the CMOS chip over-layers, by utilizing graded index optically transparent layers immediately above the Si LED emission point. FIG. 9 shows an embodiment for coupling of optical radiation as emitted from the Si LED 100 into a laterally positioned waveguide 900.

A window is wet-etched or dry-etched above the Si CMOS LED light emitting region 920, having dimensions in the micron range. This is followed by appropriately masking the rest of the plan view of the CMOS chip with a mask and then depositing various layers 910 of graded index in the cavity. If the choice of grading is chosen correct, in this case from low to high as one progress from the Si—$SiO_2$ interface towards the surface, refraction of light may be generated in two dimensions such that the emitted light is focused into the core of any single mode or multimode optical fibre, with a very good coupling coefficient.

A depletion layer 930, a carrier excitation region 940 are part of the Si LED 100, as well as second region 120, electric contact region 960 and oxide insulating layer 980, similar to the devices as described with respect to the previous embodiments.

In further embodiments, different over-layers may be deposited through masks using the same graded index concepts and definition of the optical index gradient both laterally and vertically in the over-layer, such that a series of optical graded index waveguides are formed in the over-layers of conventional CMOS integrated circuitry, by employing appropriate post-processing procedures. In further embodiments different over-layers may be deposited through masks using the same graded index concepts and definition of the optical index gradient both laterally and vertically in the over-layer, such that a series of optical graded index waveguides are formed directly on top of the insulating layer, normally the field oxide layer of CMOS IC's, such that a region of higher refractive index are formed directly above the field oxide layer, and such that a conventional rib waveguide or single or multimode mode high index fibre/waveguide are formed, and such that the emission from the Si CMOS LED effectively couple into the higher index part of the waveguide. The detail process and choice of materials can be chosen in order to optimize the technology. If necessary, optical layers may be pre-deposited before metal layers are deposited which are normally require a low thermal budget and are accommodated at the end of the CMOS processing procedure. The graded index composition can also be obtained with conventional glass doping and glass flow techniques. If necessary, certain dedicated optical modules can be separately fabricated using different processes, and pick and placed into position together with pick and placing of fibre optical modules after CMOS processing, and as a post processing procedure. All these embodiments are usually suitable for implementation with above 0.35 micron CMOS technology.

Figure 11:
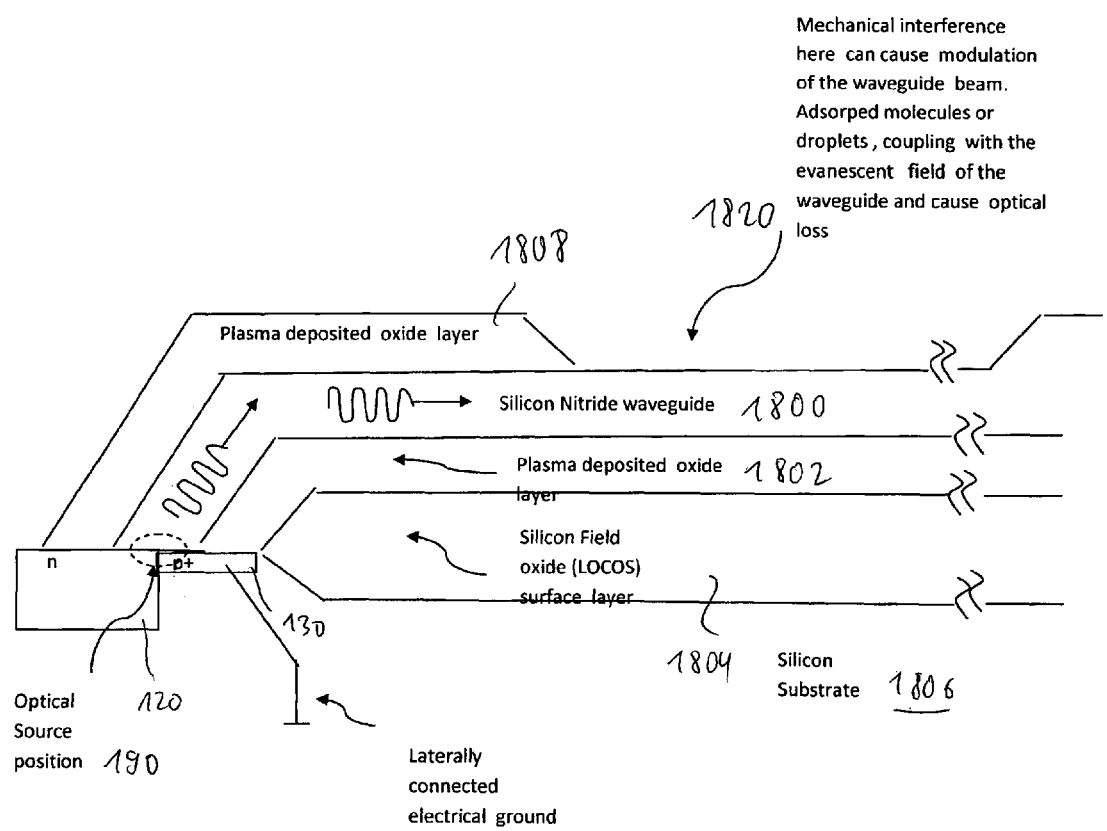
Figure 12:
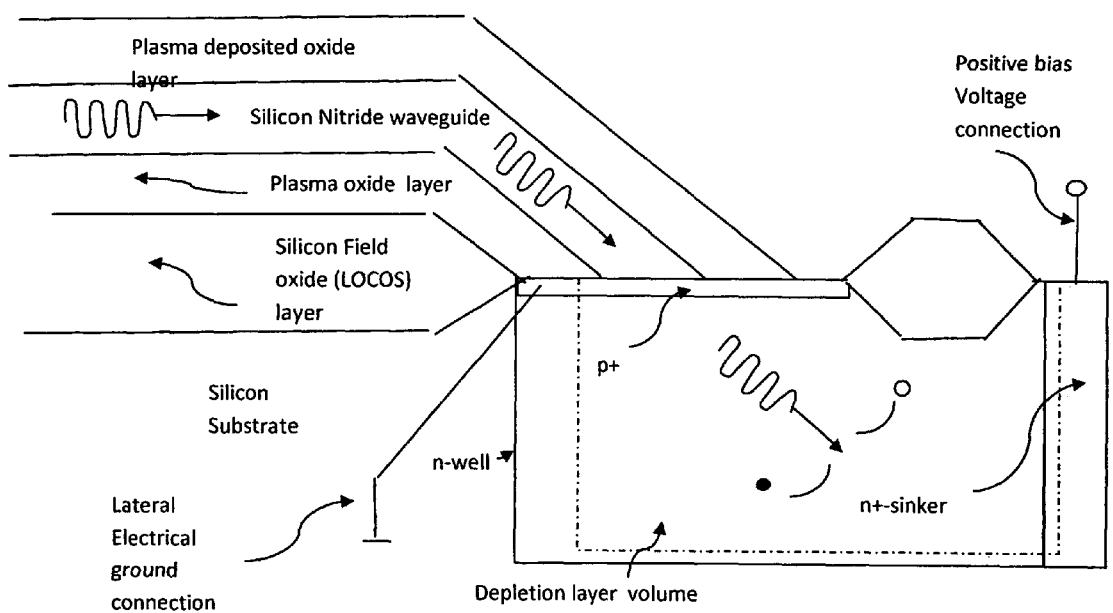

FIG. 10 to FIG. 12 shows some further preferred embodiments using above 0.35 micron CMOS technology.

In FIG. 10 the Si LED 100 according to FIG. 1 couple effectively into a 1 micron thick Si Nitride or polymer waveguide 1800. The Silicon nitride or Si-Oxinitride or polymer based waveguide 1800 coupling is realized on top of the plasma deposited 1802 and field oxide layer 1804 as is normally encountered in above 0.35 micron CMOS technology. Above the waveguide 1800, a further plasma deposited oxide layer 1808 is present, so as to embed the waveguide. Appropriate n-well 120 and p+ definitions 130 in the silicon substrate 1806 define the positioning of the light generation Zone at 190 such that optimized coupling of the light is accomplished.

FIG. 11 elaborates on this embodiment by showing a small interface area 1820 realized by means of wet or RF etching such that mechanical, chemical or adsorption process can interfere with the evanescent field as associated with the waveguide, causing excessive optical power loss in the waveguide and subsequent intensity changes. A reference optical path A may be realized in parallel to this waveguide in order to ensure as effective reference intensity and signal.

FIG. 12 shows an embodiment of a corresponding CMOS based detector elaborating on this technology. The optical detector structure can be realized with a RF pre-etching on the p+ region before deposition of the Silicon nitride layer. A p+ n-well based detector is utilized in order to provide an elongated depletion layer, 45 degrees diagonally down into the wafer for above 600 nm wavelength. This will provide greater detection efficiency of the detector when using Si nitride or high index polymer waveguides.

Figure 13:
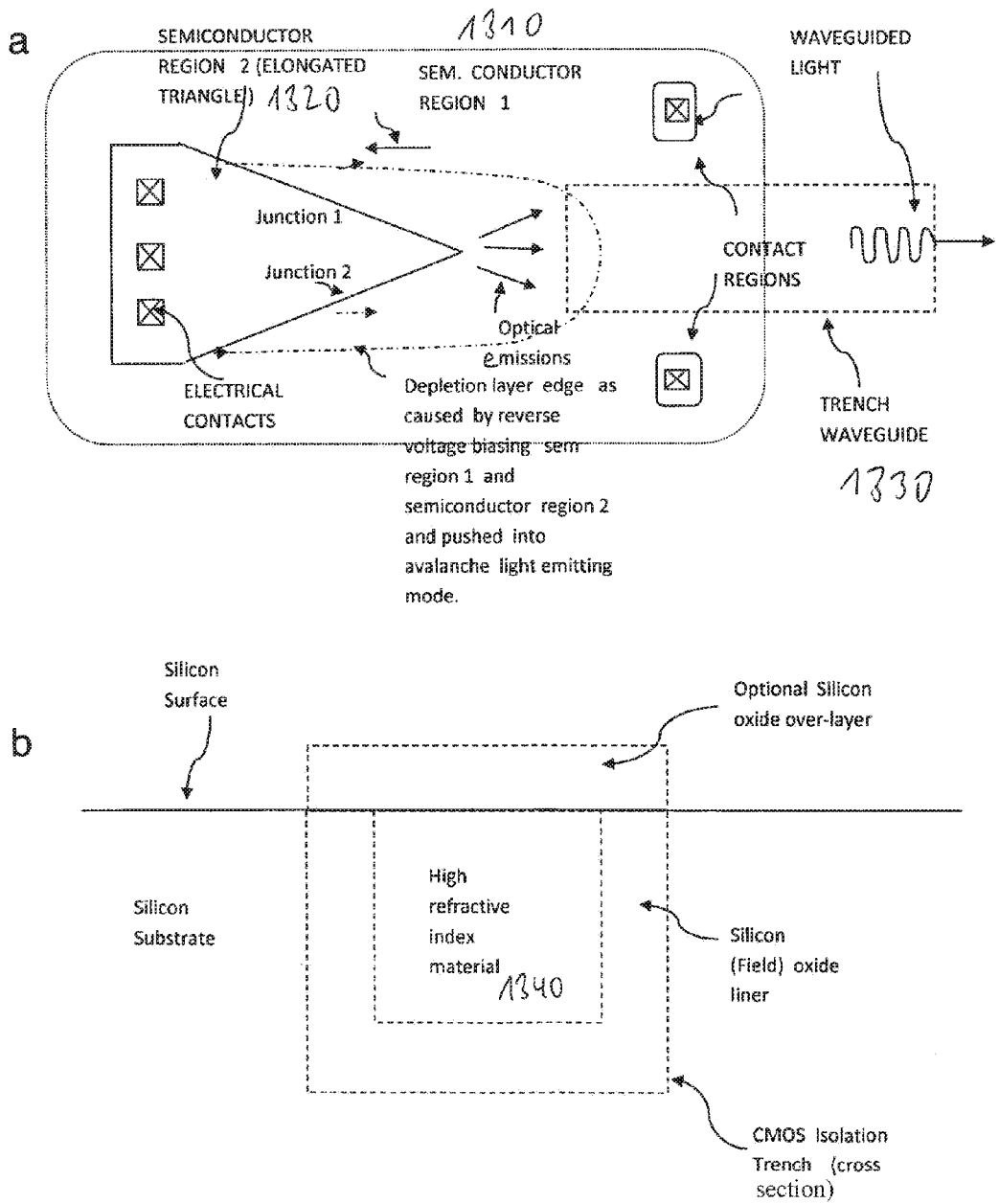
FIG. 13 show preferred embodiments of Si LED and waveguide technology as associated with the technology using below 0.35 micron CMOS technology.
Figure 14:
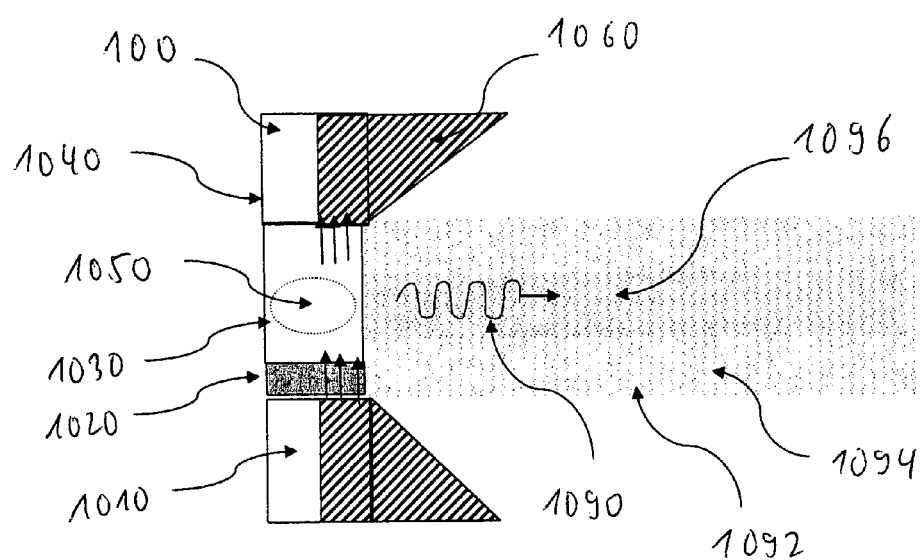
FIG. 14 shows a schematic diagram showing achievement of effective coupling of optical radiation from a Lateral Multiplication and Secondary Excitation Si LED into an isolation trench based waveguide structure which can be implemented in below 0.35 micron CMOS technology.

FIGS. 13 and 14 and show preferred embodiments of Si LED and waveguide technology as associated with the technology using below 0.35 micron CMOS technology.

FIG. 13(*a*) shows the realization of a lateral enhanced multiplication SI LED as in FIG. 1 as realized with appropriate doping layers and embedding techniques. The highly doped region 1310 is embedded in a region of lower doping 1320. The triangular tip of the highly doped region 1 is such that the light emission zone interfaces with the core of a trench-based optical waveguide 1330 positioned by separate techniques near to the waveguide structure. FIG. 13(*b*) shows a cross-section of the trench based waveguide. The trench is outlined by a thin layer of field oxide or other based silicon oxide 1330. A higher refractive index material 1340 is realized inside the trench by means of suitable technology. The core region can be of square or circular refractive index profile so as to create either single mode or multimode optical propagation according to usual optical fibre technology.

FIG. 14 shows a schematic diagram showing achievement of effective coupling of optical radiation from a Lateral Multiplication and Secondary Excitation Si LED into an isolation trench based waveguide structure which can be implemented in below 0.35 micron CMOS technology. The isolation trench which is normally used for electrical isolation purposes has been filled by suitable layers of different refractive index material, so as to form an optical waveguide along the trench in a lateral direction. FIG. 14 shows a further embodiment of the invention in order to enhance the optical coupling from the body 100 structure into the optical conducting body 1092. FIG. 14 shows a schematic representation of an embodiment of the generic E-MOD Si LED in order to enhance silicon and optical waveguide interface charge carrier interaction as well as enhancing optical coupling from the Si LED into a lateral positioned waveguide. Here the generic body 100 structure comprising three or four regions 1010 to 1040 are used, but the metal contacts and feeds are such placed on metal layer 1060 that a higher current density is favoured at the surface of second region 1020 and third region 1030, hence maximizing optical yield at the region 1020 and region 1030 surface with the optical fibre core, hence enhancing coupling of the optical radiation 1090 into the higher index core 1096 of the waveguide 1092.

Here the respective regions 1010-1040 may be embedded into each other and/or placed adjacently to each other in order to create a functional Si LED structure. The Electrical contact regions are with normal plasma deposition and etching techniques. The wave-guiding secondary optically conductive region could be fabricated by either using isolation trench technology as utilised for below 0.35 micron technology or even polymer technology. The higher core refractive index can be fabricated by modifying and trench fabrication technology. The encapsulating of the body 100 region can be achieved by first defining the silicon regions 1410 to 1440 by lithographic processes using the topmost silicon layer of the silicon on oxide on insulator structure, and then depositing/growing secondary oxide layers so as to encapsulate the initial body 100. The wave-guiding secondary optically conductive region 1094 could be fabricated by using plasma deposition, wet oxide or secondary polymer deposition techniques, such that a strip of low refractive index is generated that contacts the active light emitting regions of the body 1092 region. The higher refractive index core regions 1096 can be fabricated by the same procedures, or using techniques and technologies as commonly utilised in the optical fibre telecommunications technology. The Electrical contact regions can be fabricated with normal plasma deposition and etching techniques.

Figure 15:
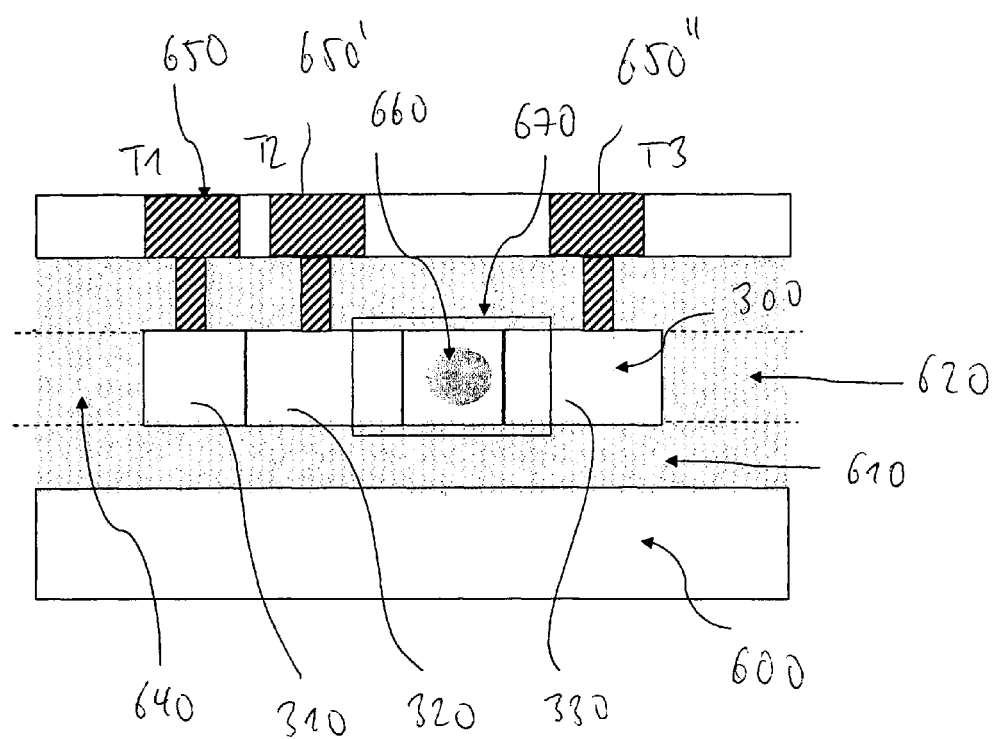
FIG. 15 shows a schematic diagram showing the realization of a MOEMS device as described in FIG. 2 by utilizing Silicon-On-Insulator (SOI) technology as further preferred embodiments of the invention.

FIG. 15 provides detail of realizing the invention in SOI technology.

FIG. 15 shows a schematic diagram showing the realization of a MOEMS device as described in FIG. 2 by utilizing Silicon-On-Insulator (SOI) technology as further preferred embodiments of the invention. The light emitting diode is fabricated in the silicon layer which is situated on top of the insulating layer. Adjacently in the same layer appropriate optical transparent waveguides are fabricated in a lateral direction which can guide the light away from the Si LED. Secondary optical paths can be generated utilizing optical splitters and also guiding the light out of the plane of the thin silicon layer.

FIG. 15 shows an embodiment of optical coupling into waveguides utilizing Silicon-On-Insulator technology in cross-sectional view. On a silicon substrate 600, a silicon oxide insulating layer 610 is formed. Above the silicon oxide insulating layer 610 a silicon layer 620 is present which can also be used for optional further active electronic components, as schematically indicated by reference numeral 640. On the silicon oxide insulating layer 610 the body 300 is formed. Here the respective regions 310, 320 330 of body 300 are defined adjacently to each other in order to create a functional Si LED structure. The p+nn+ active region is fabricated on the silicon layer 620 of the three layer silicon-on oxide on Si insulator substrate 600. The Electrical contact regions 650, 650' and 650" are realized with normal plasma deposition and etching techniques for all terminals T1, T2 and T3 contacting the respective regions 310, 320 330 of body 300.

A higher core refractive index 660 can be fabricated by modifying and trench fabrication technology. The wave-guiding secondary optically conductive region 670 could be fabricated by either using plasma deposition, wet oxide or secondary polymer deposition techniques, such that a strip of low refractive index is generated that contacts the active light emitting regions of the body 300 region, and lying in the plane of the silicon on insulator layer 620. The higher refractive index core regions 660 can be fabricated adjacently to the body 300 structure, in the same plane as the silicon layer 620, by the same procedures, or using techniques and technologies as commonly utilized in the optical fibre telecommunications technology, and according to the structural layout concepts. The waveguides and electro-optical coupling structures as realized in the embodiments as described above may utilizing either silicon oxide, silicon oxi-nitride, polymer or silicon nitride or combinations of these. The waveguides should be of suitable low loss selected, of glassy type.

As shown in FIG. 15, the respective regions as in body 300 may be embedded into each other and/or placed adjacently to each other in order to create a functional Si LED structure. The Electrical contact regions are with normal plasma deposition and etching techniques. The wave-guiding secondary optically conductive region could be fabricated by either using isolation trench technology as utilised for below 0.35 micron technology or even polymer technology. The higher core refractive index can be fabricated by modifying overlayers and trench fabrication technology. The encapsulating of the body 300 region can be achieved by first defining the silicon regions by lithographic processes using the topmost silicon layer of the silicon on oxide on insulator structure, and then depositing/growing secondary oxide layers so as to encapsulate the initial body region. The wave-guiding secondary optically conductive region could be fabricated by either using plasma deposition, wet oxide or secondary polymer deposition techniques, such that a strip of low refractive index is generated that contacts the active light emitting regions of the body region, and lying in the plane of the silicon on insulator layer. The higher refractive index core regions can be fabricated by the same procedures, or using techniques and technologies as commonly utilised in the optical fibre telecommunications technology. The Electrical contact regions can be fabricated with normal plasma deposition and etching techniques.

The waveguides and electro-optical coupling structures as realized in the embodiments as described above may utilizing either silicon oxide, silicon oxi-nitride, polymer or silicon nitride or combinations of these. The waveguides should be of suitable low loss selected, of glassy type.

Standard Si p-n and Si p-i-n detector arrangements can be utilized in the invention as detectors.

Although certain embodiments only have been described herein, it will be readily apparent to any person skilled in the art that other modifications and/or variations of the invention are possible. Such modifications and/or variations are therefore to be considered as falling within the spirit and scope of the invention as herein described and/or exemplified.

The invention claimed is:

1. A sensor device comprising:
   A Silicon-based light emitting structure operating in avalanche breakdown mode, the light emitting structure being a SiLED and capable of transmitting light having a wavelength higher than 600 nm but lower than the absorption edge of silicon at 950 nm;
   A monolithically integrated wave-guiding system integrated with the silicon light emitting structure, the wave-guiding system comprising a trench in a substrate being outlined by a thin layer of oxide and a higher refractive index material, which can be of square or circular refractive index profile so as to create either single mode or multimode optical propagation;
   An interface module introducing an intensity change and/or phase change of the transmitted light;
   A detector for detecting the intensity and/or phase change; and
   An integrated electronic driving and processing circuitry so as to process the detector output signal, so as to sense parameters such as vibration, motion, rotation, acceleration, gas flow, gas composition or liquid flow or liquid composition or to detect optical absorption, additional wavelength added or omitted elements in gaseous or fluidic samples, wherein the Silicon-based light emitting structure, the monolithically integrated wave-guiding system, the detector, and the integrated electronic driving and processing circuitry are integrated on a single chip.

2. The sensor as claimed in claim 1, which is either Complementary Metal Oxide Semiconductor (CMOS) technology based or Silicon-on-insulator (SOI) based.

3. The sensor as claimed in claim 1, further comprising additional optical filters and/or a reference optical path section so as to increase the sensitivity of the device for measurements.

4. The sensor as claimed in claim 1, wherein light of the Silicon-based light emitting structure is emitted directional.

5. The sensor as claimed in claim 1, wherein the wave-guiding system comprises a plurality of transparent layers with graded refractive indices.

6. The sensor as claimed in claim 1, wherein the trench is an isolation trench in a below 0.35 µm CMOS technology.

7. The sensor as claimed in claim 1, the wave-guiding system comprising Silicon nitride, or silicon-oxinitride or an optically transparent polymer.

8. The sensor as claimed in claim 1, wherein the light emitting structure comprises a lateral enhanced multiplication SI LED having a highly doped region which is embedded in a region of lower doping and having a triangular tip such that a light emission zone interfaces with a core of a trench-based optical waveguide.

9. The sensor as claimed in claim 1, wherein the detector is a p+n-well based detector with an elongated depletion layer, which is 45 degrees diagonally down into the wafer for above 600 nm wavelength detection.

* * * * *